United States Patent
Huang et al.

(10) Patent No.: US 6,933,380 B2
(45) Date of Patent: Aug. 23, 2005

(54) EXCIPIENTS CONTAINING LOW RESIDUAL SOLVENT AND METHOD FOR PRODUCING THE SAME

(75) Inventors: Yun-Peng Huang, Tachia (TW); Fangchan Lee, Tachia (TW); Jer-Yen Shaw, Tachia (TW)

(73) Assignee: Yung-Zip Chemical Ind. Co., Ltd., Tachia (TW)

( * ) Notice: Subject to any disclaimer, the term of this patent is extended or adjusted under 35 U.S.C. 154(b) by 0 days.

(21) Appl. No.: 09/991,978

(22) Filed: Nov. 26, 2001

(65) Prior Publication Data

US 2003/0096003 A1 May 22, 2003

Related U.S. Application Data

(60) Provisional application No. 60/330,081, filed on Oct. 19, 2001.

(51) Int. Cl.[7] ................................. C07H 1/00
(52) U.S. Cl. ................. 536/123.1; 536/30; 536/45; 536/52; 536/102; 536/114; 536/124; 424/458; 424/457; 424/461; 424/462; 424/468; 424/494; 424/497
(58) Field of Search .............. 536/30, 45, 52, 536/56, 102, 114, 124, 123.1; 424/458, 457, 461, 462, 468, 494, 497, 469, 409, 413, 465, 499

(56) References Cited

U.S. PATENT DOCUMENTS

| | | | |
|---|---|---|---|
| 5,478,571 A | * 12/1995 | Gala et al. | ................ 424/464 |
| 5,534,555 A | 7/1996 | Meggelaars et al. | |
| 5,574,150 A | 11/1996 | Yaginuma et al. | |
| 5,840,329 A | * 11/1998 | Bai | ............................ 424/458 |
| 5,989,589 A | 11/1999 | Cartilier et al. | |
| 6,063,402 A | 5/2000 | Gebert et al. | |
| 6,075,177 A | * 6/2000 | Bahia et al. | .................. 602/43 |
| 6,187,339 B1 | 2/2001 | de Haan et al. | |
| 6,217,909 B1 | 4/2001 | Sherwood et al. | |
| 6,271,278 B1 | 8/2001 | Park et al. | |

* cited by examiner

Primary Examiner—James O. Wilson
Assistant Examiner—Patrick Lewis
(74) Attorney, Agent, or Firm—Fei-Fei Chao; Bingham McCutchen LLP

(57) ABSTRACT

The present invention provides low-residual-solvent containing excipients with residual solvent less than <3000 ppm. Most of the excipients are required to first be modified to become more water absorbing such as by attaching a water absorbing radical, e.g., (—$CH_2COONa$) to the carbinol groups (—$CH_2OH$) of the excipients to form a —$CH_2$—O—$CH_2COONa$ linkage. The linkage of the water-absorbing groups to e excipients improves the water absorbing property of the excipients, which facilitates the replacing residual solvent with water. The residual solvent can be extracted from the excipient by way of mixing with a solvent/water solution containing (1) about 75–95% (v/v) isopropanol and about 5–25% water (v/v); (2) about 65–95% acetone and about 5–35% water; and (3) about 60–85% methanol and about 15–40% water.

23 Claims, No Drawings

EXCIPIENTS CONTAINING LOW RESIDUAL SOLVENT AND METHOD FOR PRODUCING THE SAME

This application claims the benefit of Provisional Application No. 60/330,081, filed Oct. 19, 2001.

FIELD OF THE INVENTION

The present invention relates to excipients, particularly disintegrants, that contain low residual solvent (<3000 ppm). The excipients are preferably polysaccharide products, which include, but are not limited to, starch, amylose, amylopectin, gelatin, starch 1500, sodium starch glycolate, cellulose, microcrystalline cellulose, hydroxypropylcellulose (HPC), carboxymethyl-cellulose (CMC), croscarmellose, hydroxypropylmethylcellulose (HPMC), and chitosan. The most favorable excipient is sodium starch glycolate. The low-residual-solvent excipient is further characterized by its water absorbing property by adding a water-absorbing radical, such as a ($-RCOO^-A^+$) (wherein $A^+$ is $Na^+$ or $K^+$; wherein R is a lower alkyl group having 1–4 carbon atoms), to the carbinol groups ($-CH_2OH$) of the excipients to form a methoxy alkylcarboxyl ($-CH_2-O-RCOO^-A^+$) group in the excipient so as to improve the water absorbing property of the excipients which facilitates the replacement of residual solvent with water. The present invention also relates to a method for reducing residual solvent in excipients. The method includes removing residual solvent from the excipients by way of adding a solventlwater solution containing: (1) about 75–95% (v/v) isopropanol and about 5–25% water (v/v); (2) about 65–95% acetone and about 5–35% water; and (3) about 60–85% methanol and about 15–40% water.

BACKGROUND OF THE INVENTION

In the pharmaceutical industry, oral administration of drugs is regarded as the most advantageous form for drug delivery. There are two major types of orally administered drug dosage forms, i.e., granules (which can be packaged into a capsule) and tablets, both are also frequently employed in non-pharmaceutical field such as fish foods, plant growth regulators, pesticides, herbicides and the like.

The simplest and most economical procedures for the manufacturing of granules and tablets are the direct grinding, granulation, and compression of all the ingredients distributed homogeneously. Usually, in addition to the blending of one or more active ingredients, at least one pharmaceutical excipient, such as a diluent, a filler, a binder, a disintegrant, a lubricant, etc., is required. An excipient is an inert and non-toxic substance added to the granules or tablets to confer a suitable consistency or form to the drug(s).

Diluents or fillers are added to increase bulk to the formulation. Lubricants are added to reduce friction during the tabletting process.

Binders are useful for grinding, granulating and/or tabletting some pharmaceutical ingredients. They provide the cohesiveness necessary for bonding together the ingredients in granules or compressing granules into tablets. Binders are especially useful in manufacturing tablets. They increase the strength of the compressed tablets and decrease the friability, leading to an improvement in the tablet appearance and mechanical characteristics. An appropriate binding agent shows flowing properties and can be blended easily.

Conventional binders include microcrystalline cellulose (Avicel PH101® and Avicel PH102®), polyvinylpyrrolidone (Kollidon®, Plasdone®), corn starch, modified starches, gums, etc. These binders are usually employed in direct compression at a concentration level of about 20% by weight. The quantity of binder used in a formulation must be carefully regulated, particularly since the tablets must disintegrate after oral administration to liberate the drug.

Disintegrants are usually added to cause the granules or compressed tablets to break immediately apart when placed in an aqueous medium. Typical disintegrants include gelatinized starches (Sta Rx®) or modified starches such as sodium starch glycolate (Primojel®). Some of these disintegrants are given the name of "superdisintegrants" because of their high efficiency, even at low concentration, and because of their high swelling capacity in the presence of water, possibly due to capillarity effect upon encounter with water.

It is known that some excipients, such as microcrystalline cellulose, present binding and disintegrating characteristics and therefore are useful both as a binder and a disintegrant.

Di- and polysaccharides, such as starch, cellulose, lactose, maltose, and sugar, are well-known to fulfil several granulation and tabletting functions, particularly as the combination of binder and filler, or binder and disintegrant. In particular, the starch products are known to be suitable in the manufacture of tablets by direct compression, whereby the powder mixture to be tabletted is introduced into the molds of a tabletting press and then compressed into tablets. For example, G. H. P. Te Wierik et al., *Pharmaceutical Research*, (1993), 10: 1274–1279, teach the preparation and use of linear dextrins, amylodextrin, metastable amylodextrins, and metastable amylose as tabletting excipients. International patent publication WO 94/01092 describes the use of low-molecular or high-molecular amylose products as tabletting excipients.

Most kinds of starch consist of granules in which two types of glucose polymers occur, i.e., amylose and amylopectin. Amylose is the unbranched type of starch that consists of glucose residues in α-1,4 linkage with an average degree of polymerization of 1000–5000 (depending on the kind of starch). Amylopectin is the branched form of starch which consists of one a α-1,6-linkage per thirty α-1,4 linkages with an average degree of polymerization of about 2,000,000. The commercially most important types of starch, i.e., corn starch, potato starch, wheat starch, and tapioca starch, contain 15–30% by weight of amylose. Of some types of cereal (barley, corn, millet, milo, rice and sorghum) and of potato starch, there exist varieties that consist substantially and completely of amylopectin. These types of starch contain less than 5% by weight of amylose and are designed by the term amylopectin starches.

Cellulose is an unbranched polymer of glucose residue joined by β-1,4-linkages. Cellulose is also well-known as a binder/disintegrant in the pharmaceutical industry. For example, U.S. Pat. Nos. 2,978,446, 3,141,875, and 3,023,104 to Battista disclose a microcrystalline form of cellulose where crystalline cellulosic aggregates are prepared in an acid medium. This product is presently sold under the tradmark of Avicel PH101® and Avicel PH102®.

Chitosan is another polysaccharide composed of repeating glucosamine units that are obtained by de-acetylation of chitin. Chitin can be obtained from exoskeletons of insects and crustacea. Chitin consists of N-acetylglucosamine in β-1,4 linkage. Thus, chitin is like cellulose except that the substituent at C-2 is an acetylated amino group rather than a hydroxyl group. Chitosan is also well-known as a binder/disintegrant.

However, in preparing either the starch or the cellulose excipients, it is a necessary step to add solvent(s) to the excipients, especially for preparing binders and disintegrants. Although the majority of the solvents are removed at the end of the preparation, a significant amount of solvents is still remained in the excipients. These residual solvents, if used in daily drug dosages for patients, may constitute a threat to and create negative effect on human health and safety.

The invention to be presented in the following sections introduces low-residual-solvent-containing (<3000 ppm) excipients and a method for preparing such low-residual-solvent-containing excipients. The low-residual-solvent-containing excipients are obtained by linking a water absorbing radical to the free carbinol group(s) on the excipients to improve the water absorbing properties of the excipients so as to replace the residual solvent with water.

SUMMARY OF THE INVENTION

The present invention provides low-residual-solvent excipients, which is characterized as having residual solvent in the excipients of less than 3000 ppm. The low-residual-solvent-containing excipients are preferably modified excipients which contain water-absorbing property. Also preferably, the low-residual-solvent excipients are polysaccharide-based material. Examples of the low-residual-solvent excipients which possess or are capable of acquiring water-absorbing property include, but are not limited to, starch based materials, cellulose based materials, sugars, Arabic gum, Guar gum etc. The preferred excipients are starch based and cellulose based materials, and chitosan. Examples of starch based materials include, but are not limited to, starch, amylose, amylopectin, gelatines, starch 1500, sodium starch glycolate. Examples of cellulose based materials include, but are not limited to, cellulose, microcrystalline cellulose, hydroxypropyl-cellulose (HPC), carboxymethyl-cellulose (CMC), croscarmellose, hydroxypropylmethyl-cellulose (HPMC). The most favorable excipient is sodium starch glycolate. Examples of the solvents which are commonly known to be present in the excipients due to preparation of the excipients, include, but are not limited to, methanol, ethanol, isopropanol, and acetone.

The water absorbing property of the low-residual-solvent excipients is obtained by linking a water absorbing radical, such as a ($-RCOO^-A^+$) (wherein $A^+$ is $Na^+$ or $K^+$; wherein R is a lower alkyl group having 1–4 carbon atoms), to the carbinol groups ($-CH_2OH$) of the excipients to form a methoxy alkylcarboxyl ($-CH_2-O-RCOO^-A^+$) group in the excipients. Hereinafter, R is referred to as lower alkyl group with 1–4 carbon atoms and $A^+$ is referred to as $Na^+$ or $K^+$. Preferably, R is a straight chain lower alkyl group. The most preferred water absorbing radical is an acetate sodium radical ($-CH_2COO^-Na^+$).

The low-residual-solvent excipients can be used in making pharmaceuticals, fish foods, plant growth regulators, pesticides, and herbicides. For pharmaceuticals, the low-residual-solvent excipients are especially advantageous for use as binders/disintegrants.

The present invention also provides a method for preparing the low-residual-solvent-containing property of the excipient, which comprises the steps of: (1) mixing a solvent/water solution with the low-residual-solvent excipient to form a solvent/water/excipient mixture; (2) removing the solvent by filtering the solvent/water/excipient mixture; and (3) drying the retained excipient to produce the low-residual-solvent excipient. There are three kinds of solvent/water solutions that can be used to extract residual solvent. They are: (1) about 75–95% (v/v) isopropanol and about 5–25% water (v/v); (2) about 65–95% acetone and about 5–35% water; and (3) about 60–85% methanol and about 15–40% water.

The residual-solvent-containing excipient is mixed with the solvent/water solution at room temperature (20–30° C.) and with high speed (about 90 rpm) agitation for a period of time, preferably for at least one hour, to sufficiently allow water to replace the residual solvent in the excipients. The residual solvent is filtered out and the remaining low-residual-solvent-containing excipient is dried using conventional drying method to remove the water from the excipient.

The modified excipients containing water-absorbing property are produced by attaching the unmodified excipient (such as potato starch) having at least a carbinol group ($-CH_2OH$) with a water absorbing radical such as ($-RCOO^-A^+$) to form a ($-CH_2-O-RCOO^-A^+$). The reaction, which results in forming a ($-CH_2-O-RCH_2-COO^-A^+$) linkage between the carbinol group of the excipient and the water absorbing radical, requires mixing the polysaccharide based material with methanol, sodium hydroxide, and a compound containing the water absorbing radical (such as $Cl-R-COO^-A^+$) at about 100° C. for about 10 hours. The water-absorbing excipient is then reacted with an acid to complete the modification process of the excipient. The preferred acid is HCl. The preferred water-absorbing compound is monochloroacetate sodium ($Cl-CH_2-COONa$).

Due to the water-absorbing characteristic of the modified excipient, when water molecules are added to the modified excipient, the residual solvent in the excipient is replaced with the water molecules, and the residual solvent can be extracted out of the excipient by filtration. The remaining wet excipient can then be dried under conventional methods.

DETAILED DESCRIPTION OF THE INVENTION

In accordance with Section 3c of the International Conference on Harmonization (ICH), entitled "Guideline on Impurities: Residual Solvents; Availability; Notice," there are three classes of solvents which are deemed to be hazardous to human health and safety (Table 1):

TABLE 1

| ICH Solvent Classification |
| --- |
| Class 1 solvents: Solvents to be avoided |
| Known human carcinogens, strongly suspected human carcinogens, and environmental hazards. |
| Class 2 solvents: Solvents to be limited |
| Non-genotoxic animal carcinogens or possible causative agents of other irreversible toxicity such as neurotoxicity or teratogenicity. Solvents suspected of other significant but reversible toxicities. |
| Class 3 solvents: Solvents with low toxic potential |
| Solvents with low toxic potential to man; no health-based exposure limit is needed. Class 3 solvents have PDEs* of 50 mg or more per day. |

*PDE = permitted daily exposure.

Two commonly used solvents, methanol and ethanol, are listed in ICH (Q3c) as class 2 (methanol) and class 3 (ethanol) solvents, with the specified level of residues shown in Table 2:

TABLE 2

Specified Residue Level of Methanol and Ethanol Under ICH (Q3c)

| | Methanol Class 2 | Ethanol Class 3 |
|---|---|---|
| ICH (Q3c) | <3000 ppm | <5000 ppm |

The classification data shown in Table 2 indicates that methanol is classified as class 2 solvent which is more biohazard than ethanol, a class 3 solvent. That is also the reason why ethanol has a tolerable level of (<5000 ppm), which is higher than that of methanol (<3000 ppm). Thus, the tolerable residual concentration for ethanol is higher than that of methanol.

The present invention provides a low-residual-solvent containing excipient, which was produced by adding a water absorbing radical from a compound such as (Cl—R—COO$^-$A$^+$) to the carbinol group (—CH$_2$OH) of the excipients to form a methyloxy-acetate (—CH$_2$—O—RCOO$^-$A$^+$) linkage between the carbinol group of the excipient and the water absorbing radical so as to improve the water absorbing property of the excipient. The preferred water absorbing radical is monochloroacetate sodium (Cl—CH$_2$COONa). The preferred excipients are polysaccharide products including their derivatives. Most favorably, the excipients are either starch based materials, cellulose based materials, or chitosan.

The following diagram illustrates how a starch or cellulose based excipient reacts with the water-absorbing radical (—CH$_2$COONa) to form the methyloxy-acetate sodium linkage between the carbinol group on the glucose residue(s) of the starch and the water absorbing radical:

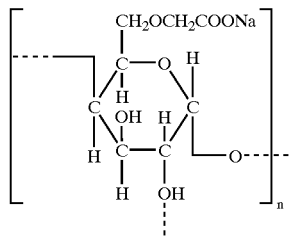

The principle behind the reduction of residual solvent from the excipient is that after the addition of the water-absorbing radical to the excipient, the excipient becomes more water-absorbing, which allows the excipient to be more acceptable to swelling/contracting when water is added to the excipient. Because the solvents (e.g., methanol, ethanol, isopropanol, or acetone) used in preparing the excipients are freely soluble in water, the subsequent addition of water to the mixture induces the replacement of the tightly bonded solvent molecules (i.e., via hydrogen bonds) within the excipient with the water molecules. The residual solvent molecules can then be extracted out of the excipient.

This solvent extraction method is particularly suitable for polysaccharide based excipient, such as starch, which is shaped in spiral helix. Small molecules such as the solvent molecules, once embedded into this type of excipient, may be tightly bonded to the excipient via hydrogen bonds and can not be extracted out from the excipient. The addition of the water absorbing group to the excipient significantly reduces the tight binding of the excipient with the solvent and allows the water molecules to be absorbed by the excipient so as to replace the solvent molecules in the excipient. As a result, the solvent molecules are extracted out of the excipient. The water molecules that are remained in the excipient can easily be eliminated by conventional drying methods.

The significance of using the solvent extraction technique in the present invention can be illustrated by comparing the residual solvent concentration in the commercially available excipient, sodium starch glycolate (a well known binder/disintegrant) with Yung Zip's DZF®, which uses the present residue extraction method (Table 3). Yung Zip's DZF® is still at the research and development stage and is not currently commercially available.

TABLE 3

Levels of Residual Solvents in Market Products of Sodium Starch Glycolate

| Manufacturer | Brand Name | Residual Solvent | Concentration (ppm) |
|---|---|---|---|
| Penwest (USA) | EXPLOTAB ® | ethanol/ethyl acetate | 41712/498 |
| Avebe (Netherlands) | PRIMOJEL ® | ethanol | 20299 |
| Blanver Farmoquimica Ltd. (Brazil) | TABLO ® | ethanol | 4575 |
| Rettenmaier (Germany) | VIVASTAR ® (P 5000) | ethanol/methanol | 346/10175 |
| Rettenmaier (Germany) | VIVASTAR ® | methanol | 5666 |
| Yung Zip (Taiwan) | DST ® | methanol | 5000 |
| Yung Zip (Taiwan) | DSF ® | methanol | 900 |

Sodium starch glycolate belongs to a group named "modified starch," which can be made from potato starch or other cereal starch (e.g., barley, corn, millet, milo, rice and sorghum). Yung Zip's DSF®'s sodium starch glycolate is made from potato starch.

The following diagram illustrates how the solvent in sodium starch glycolate can be extracted by water. Sodium starch glycolate has high disintegration and breakdown capability. It is regarded as "super disintegrants" in the pharmaceutical industry due to the amount of such compound required in drug formulation, which can be as low as 2% to 4% by weight.

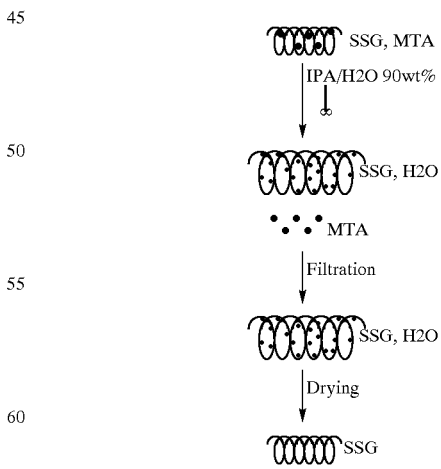

in which SSG represents the modified sodium starch glycolate which contains better water-absorbing property, MTA represents methanol, and IPA represents isopropanol. As shown in this diagram, MTA is initially bonded to the spiral helix structure of the SSG. A solvent/water mixture, which contains 90% IPA and 10% Water, is added to the SSG-MTA mixture. The solvent/water mixture and SSG (with MTA) are then agitated at high speed (approximately 90 rpm) for about 1 hour at room temperature (20–30° C.). At this stage, the MTA is dissociated from the SSG and can be extracted out from the SSG by filtration. The remaining SSG is then dried using conventional methods to produce the final dry product of SSG.

Three solvent/water mixtures are recommended to be used as the initial in the above reaction: (1) about 75–95% (v/v) isopropanol and about 5–25% water (v/v); (2) about 65–95% acetone and about 5–35% water; and (3) about 60–85% methanol and about 15–40% water.

The following examples are illustrative, and should not be viewed as limiting the scope of the present invention. Reasonable variations, such as those occur to reasonable artisan, can be made herein without departing from the scope of the present invention.

EXAMPLE 1

Preparation of Sodium Starch Glycolate from Potato Starch

Sodium starch glycolate was prepared from potato starch according to the following steps:

1. Potato starch (45 g) was mixed with methanol (90 ml), sodium hydroxide (NaOH) (3.0 g), and $ClCH_2COONa$ (10.0 g) and heated at 100° C. for ten (10) hours to attach the water-absorbing group —$CH_2COONa$ to the potato starch.
2. Methanol (10 ml) and HCl (2 ml) were added into the mixture of (1) and heated at 100° C. for ten (10) more hours.
3. An aliquot amount of NaOH was added to adjust the pH of the mixture to neutral.
4. Water 10 ml was added into the mixture of (3) and agitated for a period of time.
5. The residual solvent was filtered.
6. The solvent-free or low-residual-solvent starch was dried, passed through a sieve, and packaged for further use.

EXAMPLE 2

Preparation of Sodium Starch Glycolate from Potato Starch

Sodium starch glycolate was prepared from potato starch as followed:

1. Potato starch (45 g) was mixed with methanol (90 ml), sodium hydroxide (NaOH) (3.0 g), and $ClCH_2COONa$ (10.0 g) and heated at 100° C. for ten (10) hours to attach the water-absorbing group —$CH_2COONa$ to the potato starch.
2. Methanol (10 ml) and HCl (2.0 ml) were added into the mixture of (1) and heated at 100° C. for ten (10) more hours.
3. An aliquot amount of NaOH was added to adjust the pH of the mixture to neutral.
4. The mixture of (3) was filtered.
5. A methanol/water solution containing 90 ml of methanol and 30 ml of water was added to the wet retainant of (4) and agitated at room temperature for a period of time.
6. The mixture of (5) was filtered; the retainant was dried, passed through a sieve and packaged for further use.

EXAMPLE 3

Preparation of Sodium Starch Glycolate from Potato Starch

Sodium starch glycolate was prepared from potato starch as followed:

1. Potato starch (45 g) was mixed with methanol (90 ml), sodium hydroxide (NaOH) (3.0 g), and $ClCH_2COONa$ (10 g) and heated at 100° C. for ten (10) hours to attach the water-absorbing group —$CH_2COONa$ to the potato starch.
2. Methanol (10 ml) and HCl (2 ml) were added into the mixture of (1) and heated at 100° C. for ten (10) more hours.
3. An aliquot amount of NaOH was added to adjust the pH of the mixture to neutral.
4. The mixture of (3) was filtered.
5. An isopropanol/water solution containing 100 ml of isopropanol and 8 ml of water was added to the wet retainant of (4) and agitated at room temperature for a period of time.
6. The mixture of (5) was filtered; the retainant was dried, passed through a sieve and packaged for further use.

EXAMPLE 4

Preparation of Sodium Starch Glycolate from Potato Starch

Sodium starch glycolate was prepared from potato starch as followed:

1. Potato starch (45 g) was mixed with methanol (90 ml), sodium hydroxide (NaOH) (3.0 g), and $ClCH_2COONa$ (10 g) and heated at 100° C. for ten (10) hours to attach the water-absorbing group —$CH_2COONa$ to the potato starch.
2. Methanol (10 ml) and HCl (2 ml) were added into the mixture of (1) and heated at 100° C. for ten (10) more hours.
3. An aliquot amount of NaOH was added to adjust the pH of the mixture to neutral.
4. The mixture of (3) was filtered.
5. An acetone/water solution containing 100 ml of acetone and 15 ml of water was added to the wet retainant of (4) and agitated at room temperature for a period of time.
6. The mixture of (5) was filtered; the retainant was dried, passed through a sieve and packaged for further use.

EXAMPLE 5

Preparation of Sodium Starch Glycolate from Corn Starch

Sodium starch glycolate was prepared from cornstarch according to the following steps:

1. Corn starch (45 g) was mixed with methanol (90 ml), sodium hydroxide (NaOH) (3.0 g), and $ClCH_2COONa$ (10 g) and heated at 100° C. for ten (10) hours to attach the water-absorbing group —$CH_2COONa$ to the corn starch.
2. Methanol (10 ml) and HCl (2 ml) were added into the mixture of (1) and heated at 90° C. for ten (10) more hours.
3. An aliquot amount of NaOH was added to adjust the pH of the mixture to neutral.
4. Water 10 ml was added into the mixture of (3) and agitated for a period of time.
5. The residual solvent was filtered out.
6. The solvent-free or low-residual-solvent wet starch that remained in the retainant was dried, passed through a sieve, and packaged for further use.

EXAMPLE 6

Preparation of Sodium Starch Glycolate from Corn Starch

Sodium starch glycolate was prepared from corn starch as followed:

1. Corn starch (45 g) was mixed with methanol (90 ml), sodium hydroxide (NaOH) (3.0 g), and $ClCH_2COONa$ (10 g) and heated at 100° C. for ten (10) hours to attach the water-absorbing group $—CH_2COONa$ to the corn starch.

2. Methanol (10 ml) and HCl (2 ml) were added into the mixture of (1) and heated at 100° C. for ten (10) more hours.

3. An aliquot amount of NaOH was added to adjust the pH of the mixture to neutral.

4. The mixture of (3) was filtered.

5. A methanol/water solution containing 100 ml of methanol and 30 ml of water was added to the wet retainant of (4) and agitated for a period of time.

6. The mixture of (5) was filtered; the wet retainant was dried, passed through a sieve and packaged for further use.

EXAMPLE 7

Preparation of Sodium Starch Glycolate from Potato Starch

Sodium starch glycolate was prepared from potato starch as followed:

1. Corn starch (45 g) was mixed with methanol (90 ml), sodium hydroxide (NaOH) (3.16 g), and $ClCH_2COONa$ (9.2 g) and heated at 100° C. for ten (10) hours to attach the water-absorbing group $—CH_2COONa$ to the corn starch.

2. Methanol (10 ml) and HCl (2 ml) were added into the mixture of (1) and heated at 100° C. for ten (10) more hours.

3. An aliquot amount of NaOH was added to adjust the pH of the mixture to neutral.

4. The mixture of (3) was filtered.

5. An isopropanol/water solution containing 100 ml of isopropanol and 10 ml of water was added to the wet retainant of (4) and agitated for a period of time.

6. The mixture of (5) was filtered; the wet retainant was dried, passed through a sieve and packaged for further use.

EXAMPLE 8

Preparation of Sodium Starch Glycolate from Corn Starch

Sodium starch glycolate was prepared from corn starch as followed:

1. Corn starch (45 g) was mixed with methanol (90 ml), sodium hydroxide (NaOH) (3.0 g), and $ClCH_2COONa$ (10 g) and heated at 90° C. for ten (10) hours to attach the water-absorbing group $—CH_2COONa$ to the corn starch.

2. Methanol (10 ml) and HCl (2 ml) were added into the mixture of (1) and heated at 100° C. for ten (10) more hours.

3. An aliquot amount of NaOH was added to adjust the pH of the mixture to neutral.

4. The mixture of (3) was filtered.

5. An acetone/water solution containing 100 ml of acetone and 15 ml of water was added to the wet retainant of (4) and agitated for a period of time.

6. The mixture of (5) was filtered; the retainant was dried, passed through a sieve and packaged for further use.

EXAMPLE 9

Preparation of Low-Residual-Solvent-Containing Carboxymethylcellulose Sodium and Croscarmellose Sodium The process of making low-residual-solvent-containing carboxymethylcellulose sodium (CMC—Na) and Croscarmellose sodium includes the following steps:

1. Cellulose (45 g) was mixed with methanol (90 ml), sodium hydroxide (NaOH) (8 g), and $ClCH_2COONa$ (25 g) and heated at 100° C. for ten (10) hours to attach the water-absorbing group $—CH_2COONa$ to the cellulose.

2. Methanol (10 ml) and HCl (2 ml) were added to the mixture of (1) and heated at 100° C. for ten (10) more hours.

3. An aliquot amount of NaOH was added to adjust the pH of the mixture to neutral.

4. Water 10 ml was added into the mixture of (3); the mixture was agitated for a period of time.

5. The mixture of (4) was filtered.

6. The wet retainant was dried, passed through sieve, and packaged for further use.

EXAMPLE 10

Preparation of Low-Residual-Solvent-Containing Carboxymethylcellulose Sodium and Croscarmellose Sodium Low-residual-solvent-containing carboxymethylcellulose sodium (CMC—Na) or Croscarmellose sodium was prepared from cellulose as followed:

1. Cellulose (45 g) was mixed with methanol (90 ml), sodium hydroxide (NaOH) (8 g), and $ClCH_2COONa$ (25 g) and heated at 100° C. for ten (10) hours to attach the water-absorbing group $—CH_2COONa$ to the cellulose.

2. Methanol (10 ml) and HCl (2 ml) were added to the mixture of (1) and heated at 100° C. for ten (10) more hours.

3. An aliquot amount of NaOH was added to adjust the pH of the mixture to neutral.

4. The mixture of (3) was filtered.

5. A methanol/water solution containing 90 ml of methanol and 30 ml of water was added to the wet retainant of (4) and agitated for a period of time.

6. The mixture of (5) was filtered; the wet retainant was dried, passed through a sieve and packaged for further use.

EXAMPLE 11

Preparation of Low-Residual-Solvent-Containing Carboxymethylcellulose Sodium and Croscarmellose Sodium Low-residual-solvent-containing carboxymethylcellulose sodium (CMC—Na) or croscarmellose sodium was prepared from cellulose as followed:

1. Cellulose (45 g) was mixed with methanol (90 ml), sodium hydroxide (NaOH) (8 g), and $ClCH_2COONa$ (25 g) and heated at 100° C. for ten (10) hours to attach the water-absorbing group $—CH_2COONa$ to the cellulose.

2. Methanol (10 ml) and HCl (2 ml) were added to the mixture of (1) and heated at 100° C. for ten (10) more hours.

3. An aliquot amount of NaOH was added to adjust the pH of the mixture to neutral.

4. The mixture of (3) was filtered.

5. An isopropanol/water solution containing 100 ml of isopropanol and 10 ml of water was added to the wet retainant of (4) and agitated for a period of time.

6. The mixture of (5) was filtered; the wet retainant was dried, passed through a sieve and packaged for further use.

EXAMPLE 12

Preparation of Low-Residual-Solvent-Containing Carboxymethylcellulose Sodium and Croscarmellose Sodium Low-residual-solvent-containing carboxymethylcellulose sodium (CMC—Na) or croscarmellose sodium was prepared from cellulose as followed:

1. Cellulose (45 g) was mixed with methanol (90 ml), sodium hydroxide (NaOH) (8 g), and ClCH$_2$COONa (25 g) and heated at 100° C. for ten (10) hours to attach the water-absorbing group —CH$_2$COONa to the cellulose.

2. Methanol (10 ml) and HCl (2 ml) were added to the mixture of (1) and heated at 100° C. for ten (10) more hours.

3. An aliquot amount of NaOH was added to adjust the pH of the mixture to neutral.

4. The mixture of (3) was filtered.

5. An acetone/water solution containing 100 ml of acetone and 15 ml of water was added to the wet retainant of (4) and agitated for a period of time.

6. The mixture of (5) was filtered; the retainant was dried, passed through a sieve and packaged for further use.

EXAMPLE 13

Preparation of Low-Residual-Solvent-Containing Starch 1500 from Corn Starch

Starch 1500 is gelatinized starch. It differs from potato starch/corn starch/cellulose for its possession good water absorbing property. Therefore, the preparation of low-residual-solvent-containing starch 1500 does not require the attachment of the water absorbing radical (—CH$_2$COONa) to corn starch. The preparation process includes the following steps:

1. Corn starch (50 g) was mixed with a solvent/water solution containing 100 ml of isopropanol and 50 ml of water. The mixture was heated at 100° C. for a period of time. Under this condition, corn starch became pasty.

2. Then, isopropanol (150 ml) was added to the mixture of (1), which was agitated for a period of time at 100° C.

3. The mixture was filtered after being cooled down.

4. A methanol/water solution containing 90 ml of methanol and 30 ml of water was added to the wet retainant of (3) and agitated for a period time.

5. The mixture of (4) was filtered.

6. The wet retainant of (5) was dried, passed through a sieve, and packaged for further use.

EXAMPLE 14

Preparation of Low-Residual-Solvent-Containing Starch 1500 from Corn Starch

Starch 1500 was prepared from corn starch of the present invention with reduced residual solvent level, the process was as follows:

1. Corn starch (50 g) was mixed with a solvent/water solution containing 100 ml of isopropanol and 50 ml of water. The mixture was heated at 100° C. for a period of time. Under this condition, corn starch became pasty.

2. Then, isopropanol (150 ml) was added to the mixture of (1), which was agitated for a period of time at 100° C.

3. The mixture was filtered after being cooled down.

4. An isopropanol/water solution containing 100 ml of isopropanol and 10 ml of water was added to the wet retainant of (3) and agitated a period of time.

5. The mixture of (4) was filtered.

6. The wet retainant of (5) was dried, passed through a sieve, and packaged for further use.

EXAMPLE 15

Preparation of Low-Residual-Solvent-Containing Starch 1500 from Corn Starch

Starch 1500 was prepared from corn starch of the present invention with reduced residual solvent level, the process was as follows:

1. Corn starch (50 g) was mixed with a solvent/water solution containing 100 ml of isopropanol and 50 ml of water. The mixture was heated at 100° C. for a period of time. Under this condition, corn starch became pasty.

2. Then, isopropanol (150 ml) was added to the mixture of (1), which was agitated for a period of time at 100° C.

3. The mixture was filtered after being cooled down.

4. A solvent/water solution containing 100 ml of acetone and 15 ml of water was added to the wet retainant of (3) and agitated for a period of time.

5. The mixture of (4) was filtered.

6. The wet retainant of (5) was dried, passed through a sieve, and packaged for further use.

EXAMPLE 16

Preparation of Low-Residual-Solvent-Containing Water-Soluble Chitosan from Chitosan Chitosan is composed of repeating glucosamine units which are obtained by de-acetylation of chitin. Chitosan is well known as a binder/disintegrant. Low-residual-solvent-containing water soluble chitosan was prepared from chitosan by adding the water-absorbing radical (—CH2COONa) to the carbinol group of the glucosamine units of chitosan to form the chemical structure as follows:

[Chemical structure diagram of chitosan derivative showing three glucosamine units with CH$_2$OH, CH$_2$OCH$_2$COONa, and CH$_2$OH substituents and NH$_2$ groups]

The process for making water-soluble chitosan of the present invention with low residual solvent was as follows:

1. Chitosan (10 g) was mixed with isopropanol (200 ml) and NaOH solution (a mixture of 7 g NaOH and 10 ml water) and heated at 90° C. for several hours.

2. ClCH$_2$COOH (4 g) was added to the mixture of (1) and the mixture was heated at 90° C. for several hours.

3. Additional ClCH$_2$COOH (4 g) was added to the mixture of (2) and the mixture was heated at 90° C. for several hours.

4. NaOH (4 g) was added to the mixture of (3) and the mixture was heated at 90° C. for several hours.

5. Additional ClCH$_2$COOH (4 g) was added to the mixture and the mixture was heated at 90° C. for several hours.

6. Water (15 ml) was added to the mixture; the mixture was agitated for a period of time.

7. The mixture of (6) was filtered to remove residual solvent.

8. The wet retainant was dried, passed through sieve, and packaged for further use.

EXAMPLE 17

Preparation of Low-Residual-Solvent-Containing Water-Soluble Chitosan from Chitosan The process for making water-soluble chitosan of the present invention with low residual solvent was as follows:

1. Chitosan (10 g) was mixed with isopropanol (200 ml) and NaOH solution (a mixture of 7 g NaOH and 10 ml water) and heated at 90° C. for several hours.

2. ClCH$_2$COOH (4 g) was added to the mixture of (1) and the mixture was heated at 90° C. for several hours.

3. Additional ClCH$_2$COOH (4 g) was added to the mixture of (2) and the mixture was heated at 90° C. for several hours.

4. NaOH (4 g) was added to the mixture of (3) and the mixture was heated at 90° C. for several hours.

5. Additional ClCH$_2$COOH (4 g) was added to the mixture and the mixture was heated at 90° C. for several hours.

6. The mixture of (5) was filtered after being cooled down.

7. A methaol/water solution containing 100 ml of methanol and 30 ml of water was added to the wet retainant of (6) and agitated for a period of time.

8. The mixture of (7) was dried, passed through a sieve, and packaged for further use.

EXAMPLE 18

Preparation of Low-Residual-Solvent-Containing Water-Soluble Chitosan from Chitosan The process for making water-soluble chitosan of the present invention with low residual solvent was as follows:

1. Chitosan (10 g) was mixed with isopropanol (200 ml) and NaOH solution (a mixture of 7 g NaOH and 10 ml water) and heated at 90° C. for several hours.

2. ClCH$_2$COOH (4 g) was added to the mixture of (1) and the mixture was heated at 90° C. for several hours.

3. Additional ClCH$_2$COOH (4 g) was added to the mixture of (2) and the mixture was heated at 90° C. for several hours.

4. NaOH (4 g) was added to the mixture of (3) and the mixture was heated at 90° C. for several hours.

5. Additional ClCH$_2$COOH (4 g) was added to the mixture and the mixture was heated at 90° C. for several hours.

6. The mixture of (5) was filtered after being cooled down.

7. An isopropanol/water solution containing 100 ml of isopropanol and 12 ml of water was added to the wet retainant of (6) and agitated for a period of time.

8. The mixture of (7) was dried, passed through a sieve, and packaged for further use.

EXAMPLE 19

Preparation of Low-Residual-Solvent-Containing Water-Soluble

Chitosan from Chitosan

The process for making water-soluble chitosan of the present invention with low residual solvent was as follows:

1. Chitosan (10 g) was mixed with isopropanol (200 ml) and NaOH solution (a mixture of 7 g NaOH and 10 ml water) and heated at 90° C. for several hours.

2. ClCH$_2$COOH (4 g) was added to the mixture of (1) and the mixture was heated at 90° C. for several hours.

3. Additional ClCH$_2$COOH (4 g) was added to the mixture of (2) and the mixture was heated at 90° C. for several hours.

4. NaOH (4 g) was added to the mixture of (3) and the mixture was heated at 90° C. for several hours.

5. Additional ClCH$_2$COOH (4 g) was added to the mixture and the mixture was heated at 60° C. for several hours.

6. The mixture of (5) was filtered after being cooled down.

7. An acetone/water solution containing 110 ml of acetone and 15 ml of water was added to the wet retainant of (6) and agitated for a period of time.

8. The mixture of (7) was dried, passed through a sieve, and packaged for further use.

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

We claim:

1. A low-residual-solvent excipient which has residual solvent of less than 3000 ppm;

wherein said low-residual-solvent excipient possesses a water absorbing property which is characterized by the presence of a methoxy alkylcarboxyl (—CH$_2$—O—RCOO$^-$A$^+$) group in said excipient;

wherein R is a lower alkyl group having 1–4 carbon atoms; wherein A$^+$ is Na$^+$ or K$^+$; and said low-residual solvent excipient being produced by mixing an excipient possessing said water absorbing property with a solvent/water solution which contains no more than 40% by volume of water to form a solvent/water/excipient mixture; filtering said solvent/water/excipient mixture to obtain a water-containing low-residual-solvent excipient; and driving said water-containing low-residual-solvent excipient to obtain said low-residual solvent excipient.

2. The low-residual-solvent excipient according to claim 1, wherein said low-residual-solvent excipient is a polysaccharide based material.

3. The low-residual-solvent excipient according to claim 2, wherein said polysaccharide based material is one selected from the group consisting of starch based material, cellulose based material, chitin based material, sugar, Arabic gum, and Guar gum.

4. The low-residual-solvent excipient according to claim 3, wherein said starch based material is one selected from the group consisting of starch, amylose, amylopectin, gelatin, and sodium starch glycolate.

5. The low-residual-solvent excipient according to claim 3, wherein said cellulose based material is one selected from the group consisting of cellulose, microcrystalline cellulose, hydroxypropyl cellulose, carboxymethyl cellulose, croscarmellose, and hydroxypropyl-methyl-cellulose.

6. A low-residual-solvent excipient which has residual solvent of less than 3000 ppm;

wherein said excipient possesses water absorbing property which is characterized by the presence of a methoxy alkylcarboxyl (—CH$_2$—O—RCOO$^-$A$^+$) group in said excipient;

wherein R is a lower alkyl group having 1–4 carbon atoms; wherein A$^+$ is Na$^+$ or K$^+$, wherein said excipient is chitosan.

7. The low-residual-solvent excipient according to claim 1, wherein said residual solvent is at least one selected from the group consisting of methanol, ethanol, isopropanol, and acetone.

8. The low-residual-solvent excipient according to claim 2, wherein said methoxy alkylcarboxyl (—CH$_2$—O—RCOO$^-$A$^+$) group of said excipient is obtained by reacting a carbinol group (—CH$_2$OH) of said excipient with a water absorbing radical.

9. The low-residual-solvent excipient according to claim 8, wherein said water absorbing radical is a —R—COO$^-$A$^+$ radical, wherein R is a lower alkyl group having 1–4 carbon atoms; wherein A$^+$ is Na$^+$ or K$^+$.

10. The low-residual-solvent excipient according to claim 9, wherein said (—R—COO⁻A⁺) radical is an acetate sodium radical (—CH₂COONa).

11. The low-residual-solvent excipient according to claim 1, wherein said low-residual-solvent excipient is used in at least one selected from the group consisting of fish foods, plant growth regulators, pesticides and herbicides.

12. A method for producing a low-residual-solvent excipient, comprising:

mixing a solvent/water solution with an excipient possessing a water absorbing property which is characterized by the presence of a methoxy alkylcarboxyl (—CH₂—O—RCOO⁻A⁺) group to form a solvent/water/excipient mixture; wherein said solvent/water solution contains no more than 40% by volume of water;

filtering said solvent/water/excipient mixture to obtain a water-containing low-residual-solvent excipient; and drying said water-containing low-residual-solvent excipient to produce said low-residual-solvent excipient.

13. The method according to claim 12, wherein said solvent/water solution is one selected from the group consisting of isopropanol/water, acetone/water, and methanol/water.

14. The method according to claim 13, wherein said isopropanol/water solution having 75–95% by volume of isopropanol and 5–25% by volume of water.

15. The method according to claim 13, wherein said acetone/water solution has 65–95% by volume of acetone and 5–35% by volume of water.

16. The method according to claim 13, wherein said methanol/water solution has 60–85% by volume of methanol and 15–40% by volume of water.

17. The method according to claim 12, wherein said solvent/water solution and said excipient is mixed at about 20 to 30° C. and with high-speed agitation.

18. The method according to claim 17, wherein said high speed agitation is at least at 90 rpm.

19. The method according to claim 12, wherein said excipient is a polysaccharide based material;

wherein said methoxy alkylcarboxyl group of said excipient is obtained by attaching a (—RCOO⁻A⁺) radical to said excinient; wherein A⁺ is Na⁺ or K⁺; wherein R is a lower alkyl group having 1–4 carbon atoms; and wherein said (—RCOO⁻A⁺) radical is attached to a carbinol (—CH₂OH) group of said excipient to form said (—CH₂—O—R—COO⁻A⁺) linkage.

20. The method according to claim 19, wherein said (—CH₂—O—R—COO⁻A⁺) linkage is produced by mixing said excipient with methanol, sodium hydroxide, and a (Cl—R—COO⁻A⁺) at about 100° C. for about 10 hours.

21. The method according to claim 20, wherein said (Cl—R—COO⁻A⁺) is a monochioroacetate sodium (Cl—CH₂—COONa).

22. A low-residual-solvent excipient which has residual solvent of less than 3000 rpm and possesses water absorbing property which is characterized by the presence of a methoxy alkylcarboxyl (—CH₂—O—RCOO⁻A⁺) group in said excipient; wherein R is a lower alkyl aroup having 1–4 carbon atoms; wherein A⁺ is Na⁺ or K⁺; and wherein said low-residual-solvent excipient is a gelatinized starch.

23. The low-residual-solvent excipient which has residual solvent according to claim 22, wherein said gelatinized starch is starch 1500 from corn starch.

* * * * *